United States Patent
Vogt et al.

(10) Patent No.: US 10,023,835 B2
(45) Date of Patent: Jul. 17, 2018

(54) METHOD OF ADJUSTING THE CONDITIONS OF BIOLOGICAL PROCESSES AND A REACTOR FOR CARRYING OUT THE METHOD

(71) Applicant: UNIWERSYTET WROCLAWSKI, Wroclaw (PL)

(72) Inventors: Andrzej Vogt, Wroclaw (PL); Stanislaw Strzelecki, Wroclaw (PL); Slawomir Jablonski, Wroclaw (PL); Marcin Lukaszewicz, Wroclaw (PL)

(73) Assignee: UNIWERSYTET WROCLAWSKI, Wroclaw (PL)

( * ) Notice: Subject to any disclaimer, the term of this patent is extended or adjusted under 35 U.S.C. 154(b) by 44 days.

(21) Appl. No.: 14/832,018

(22) Filed: Aug. 21, 2015

(65) Prior Publication Data

US 2016/0060590 A1    Mar. 3, 2016

(30) Foreign Application Priority Data

Sep. 1, 2014  (PL) .......................................... 409342
Sep. 1, 2014  (PL) .......................................... 409343

(51) Int. Cl.
| | | |
|---|---|---|
| *C12P 19/24* | (2006.01) | |
| *C12M 1/42* | (2006.01) | |
| *C12M 3/00* | (2006.01) | |
| *C12M 1/36* | (2006.01) | |
| *C12M 1/38* | (2006.01) | |
| *C12M 1/34* | (2006.01) | |
| *C12M 1/06* | (2006.01) | |

(52) U.S. Cl.
CPC ............ *C12M 41/26* (2013.01); *C12M 27/02* (2013.01); *C12M 35/02* (2013.01); *C12M 41/28* (2013.01); *C12M 41/48* (2013.01)

(58) Field of Classification Search
None
See application file for complete search history.

(56) References Cited

U.S. PATENT DOCUMENTS

| | | | |
|---|---|---|---|
| 2,322,545 A | | 6/1943 | Sandstrom |
| 2,567,257 A | * | 9/1951 | Voss .......................... C12N 1/16 426/31 |
| 3,065,156 A | | 11/1962 | Lewin et al. |
| 5,443,706 A | * | 8/1995 | Kuroda ................... C02F 3/005 204/242 |
| 6,669,849 B1 | * | 12/2003 | Nguyen ................... B01J 39/04 210/638 |
| 2004/0241771 A1 | * | 12/2004 | Zeikus ..................... C02F 3/005 435/7.32 |
| 2005/0070004 A1 | * | 3/2005 | Ishizaki .................... C12N 1/20 435/252.1 |
| 2006/0073577 A1 | * | 4/2006 | Ka-Yiu ...................... C12P 7/40 435/106 |
| 2008/0308421 A1 | | 12/2008 | Gratzl et al. |

FOREIGN PATENT DOCUMENTS

JP             62134550 A     6/1987

OTHER PUBLICATIONS

Garbacz et al., AAPS PharmSciTech, vol. 14, No. 2, Jun. 2013.*

* cited by examiner

*Primary Examiner* — Thomas J. Visone
(74) *Attorney, Agent, or Firm* — Andrew W. Chu; Craft Chu PLLC

(57) ABSTRACT

The method of pH controlling during electrolytic fermentation processes of the organic substrates includes placing the biological and chemical reagents in a fermentation tank, placing the electrodes powered by the direct current in the fermentation tank chambers, switching on the constant voltage initiating electrolytic processes with a value from 0.1 to 50 V, generating H+ or OH− ions around the electrodes, reading the data from the glass electrode, changing the power parameters of electrodes, depending on the set pH value of the reaction medium, and starting a pump metering the liquid from the auxiliary chamber into the fermentation tank chamber through a dispensing connector. The object of the invention is also the reactor for carrying out this method.

5 Claims, 4 Drawing Sheets

METHOD OF ADJUSTING THE CONDITIONS OF BIOLOGICAL PROCESSES AND A REACTOR FOR CARRYING OUT THE METHOD

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The object of the invention is the method of controlling pH of the medium in the fermentation processes in an aqueous medium and a reactor for carrying out this process. The object of the invention can be used in electrolytic processes of fermentation carried out in an aqueous medium.

2. Description of Related Art Including Information Disclosed Under 37 CFR 1.97 and 37 CFR 1.98.

The systems used to carry out fermentation with microorganisms are made of reactors connected with the devices providing controlled conditions for the growth of microorganisms. In these systems the parameters such as: pH and availability of nutrients are adjusted using a set for dispensing fluids (gases or liquids) overcoming certain medium changes caused by the activity of microorganisms.

A microbiological culture is often accompanied by a change of pH resulting from producing acidic or alkaline substances or getting them from the substrate. Because, to a large extent, life processes of microorganisms depend on the growth conditions, pH should be adjusted in order to maintain culture performance.

In the standard approach, adjustment of pH of the medium while carrying out fermentation processes is based on the system consisting of a sensor (glass electrode with a pH meter) connected to a decision-making unit (microprocessor system) and a peripheral device (pump) metering a concentrated solution of a neutralizing agent (acid or base). The neutralizing agent is fed to the reactor if the sensor registers exceeding the setpoint by the operator.

U.S. Pat. No. 7,250,288B2 shows the concept of using the electrodes with immobilized biological catalyst (whole microorganisms or enzymes) as a method for providing reduction power for conducting enzymatic reactions or fermentation processes.

U.S. Pat. No. 5,443,706A uses a similar solution for treating wastewater of nutrients. The reactor equipped with an appropriate set of electrodes was used for the biological reduction of nitrate into free nitrogen from aqueous solutions using the reduction power provided by the electrodes. Thanks to the same solution, it was also possible to produce methane through carbon dioxide reduction. Both processes used cultures of microorganisms of appropriate metabolic capacity.

SUMMARY OF THE INVENTION

The reactor of the invention is intended for culturing microorganisms under controlled conditions, with a computer-controlled electrolytic and/or hydraulic system.

The reactor comprises a fermentation tank and an auxiliary tank connected with a salt bridge (allowing the flow of ions while minimizing the mixing of the solutions). A glass electrode measuring the pH changes in the medium and an electrode being a part of the electrolyzing system are introduced into the fermentation tank through a hole in the upper cover. A second electrode of the electrolyzing system is introduced into the auxiliary chamber. Electrodes of the electrolyzing system are connected to a direct current power supply. Depending on available materials, the electrodes can be made of stainless steel, coal, ceramic sintered composites sprayed with a metal or graphite layer. Additionally, the electrodes (both or only one of them) may be set into a rotating motion in order to reduce the layer of ions accumulated thereon. Capacity control of the reactor can be achieved in several ways: for example, switching on, power and polarization can be controlled by a control computer based on the readings from pH measurement system. Another option is to correct the pH changes by transferring the liquid from the auxiliary chamber into the fermentation chamber through a computer-controlled pump while the electrolyzing system is in constant operation.

The fermentation chamber may be equipped with a mixer, a temperature sensor and a heat source (a heater or a water jacket) necessary to maintain a constant temperature of fermentation and ports allowing for the introduction of fluids, sampling and receiving gaseous products of fermentation conventionally used in the construction of bioreactors.

The essence of the invention is the method of pH controlling during electrolytic fermentation processes of the organic substrates, characterized in that it comprises the following steps:

placing the biological and chemical reagents in the fermentation tank, placing the electrodes powered by the direct current in the fermentation tank chambers, switching on the constant voltage initiating electrolytic processes with a value from 0.1 to 50 V, generating H+ or OH− ions around the electrodes, reading the data from the glass electrode, changing the power parameters of electrodes, depending on the set pH value of the reaction medium, starting a pump metering the liquid from the auxiliary chamber into the fermentation camber through a dispensing connector.

Preferably, changing the power parameters of electrodes depending on the set pH value of the reaction medium consists in the fact that in the medium with pH <7, the first electrode is polarized negatively and the other electrode is polarized positively.

Preferably, changing the power parameters of electrodes depending on the set pH value of the reaction medium consists in the fact that in the medium with pH >7, the first electrode is polarized positively and the other electrode is polarized negatively.

Preferably, in the medium with pH<7, OH− ions are generated around the electrode.

Preferably, in the medium with pH>7, H+ ions are generated around the electrode.

The object of the invention is also a reactor for carrying out electrolytic fermentation processes of the organic substrates, comprising at least one fermentation tank equipped with an electrode powered by a direct current power supply characterized in that pH of the reaction mixture is controlled by generating H+ or OH− ions around the electrodes as a result of switching on direct electric current.

Preferably, the reactor tanks are a part of the fermentation chamber connected to the auxiliary chamber through a salt bridge.

Preferably, the first electrode disposed in the reactor fermentation chamber is driven by a motor, whereas the second electrode is disposed in the auxiliary chamber.

Preferably, the electrode functions as a mixer.

Preferably, the reactor comprises a pump metering the liquid from the auxiliary chamber into the fermentation chamber through a dispensing connector.

Preferably, the direct current power supply of the reactor is controlled by the control device based on the indications of the glass electrode.

DETAILED DESCRIPTION OF THE DRAWINGS

Use of the reactor according to the invention allows to control pH of the medium in the fermentation chamber without adding neutralizing substances, but only through the process of electrolysis of water.

A characteristic feature of the reactor is the design permitting the use of pH changes of the medium which accompany the process of electrolysis of water to control pH while culturing microorganisms in an aqueous medium. The current flow through the electrolyzing system causes the movement of ions between the chambers of the device, preventing the pH change of the substrate in the reactor resulting from the exudation of acidic or alkaline metabolites by the microorganisms into the substrate. Therefore, an appropriately controlled electrolyzing system applied in the reactor may successfully replace conventional solutions used to control the pH of the reaction in bioreactors.

The reactor of the invention, devoid of the conventional system of pH control based on dispensing neutralizing substances, allows to control the pH changes during fermentation, especially when it is desirable to avoid an increase in the salinity of the substrate. Graphs shown in FIG. 4 and FIG. 5 present that pH of the solution (for the control sample with no voltage applied onto the electrodes, FIG. 4) decreases when the fermentation process progresses, whereas when the voltage is applied onto the electrodes and $OH^-$ ions around the electrodes in the fermentation chamber and $H^+$ ions in the auxiliary chamber are generated, pH increases to baseline.

In the particular example of methane fermentation, an additional benefit resulting from the application of the said system, besides pH adjustment, is the increase of the methane content in the resultant biogas through the use of hydrogen (mainly as "in statu nascendi") generated at the cathode for the reduction of carbon dioxide.

Figure 1:
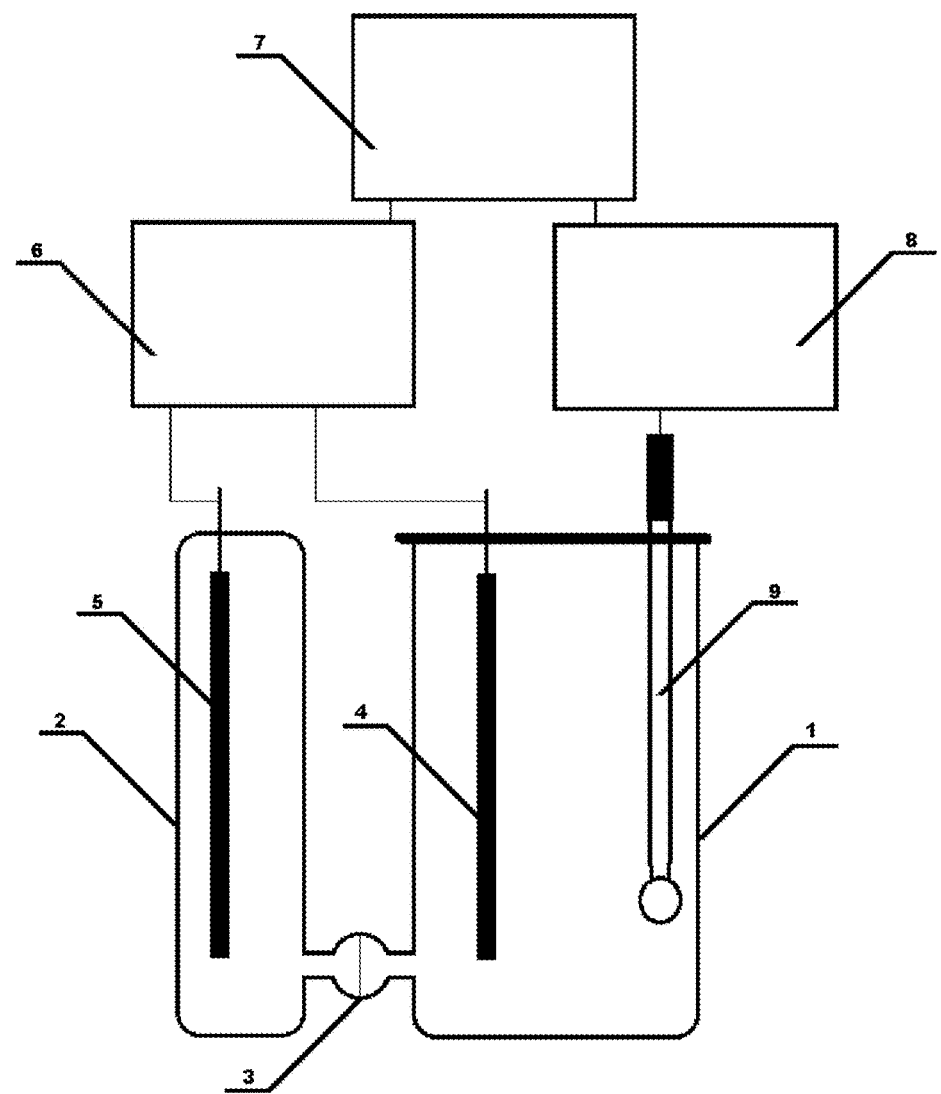
FIG. 1 is a schematic view of an embodiment of present invention.
Figure 2:
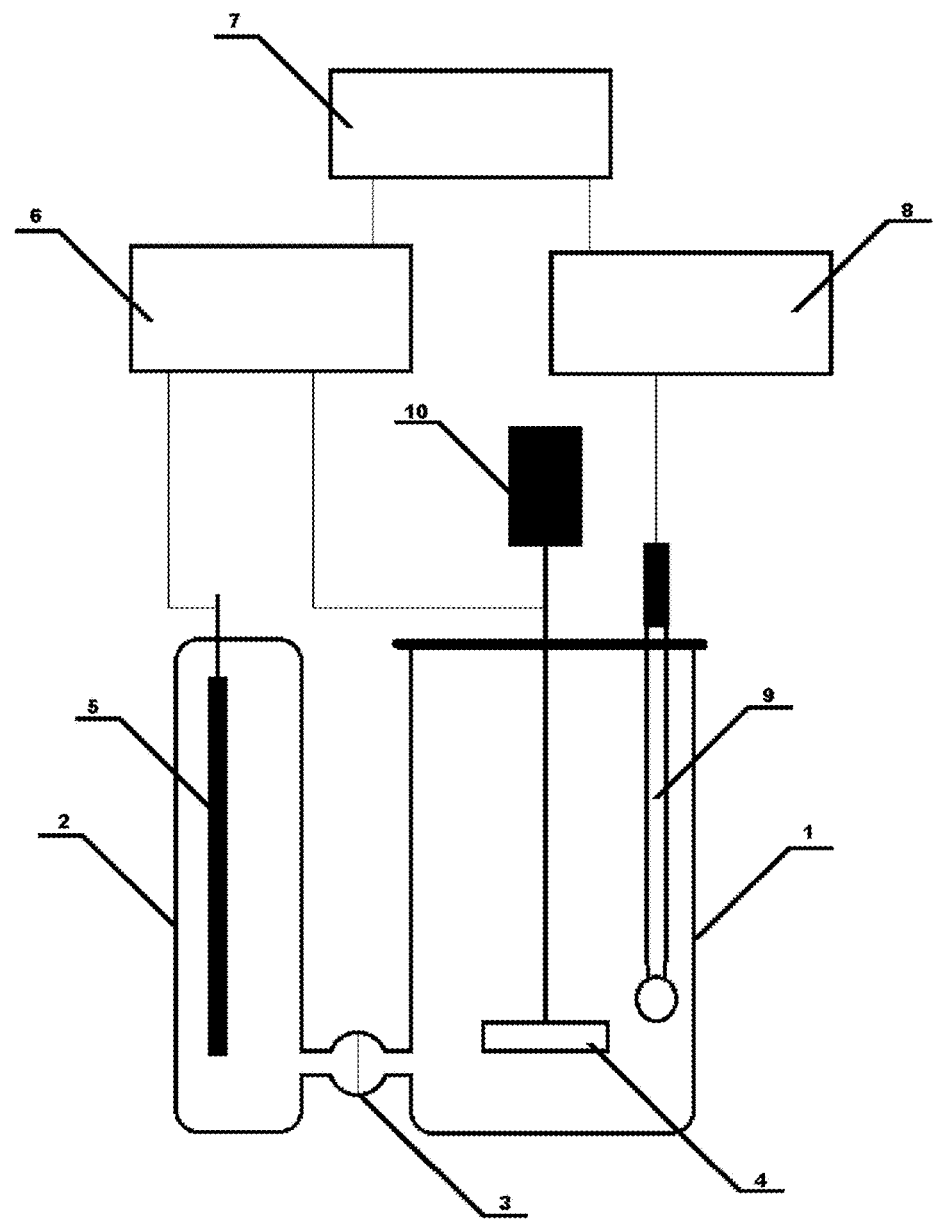
FIG. 2 is another schematic view of an embodiment of the present invention.
Figure 3:
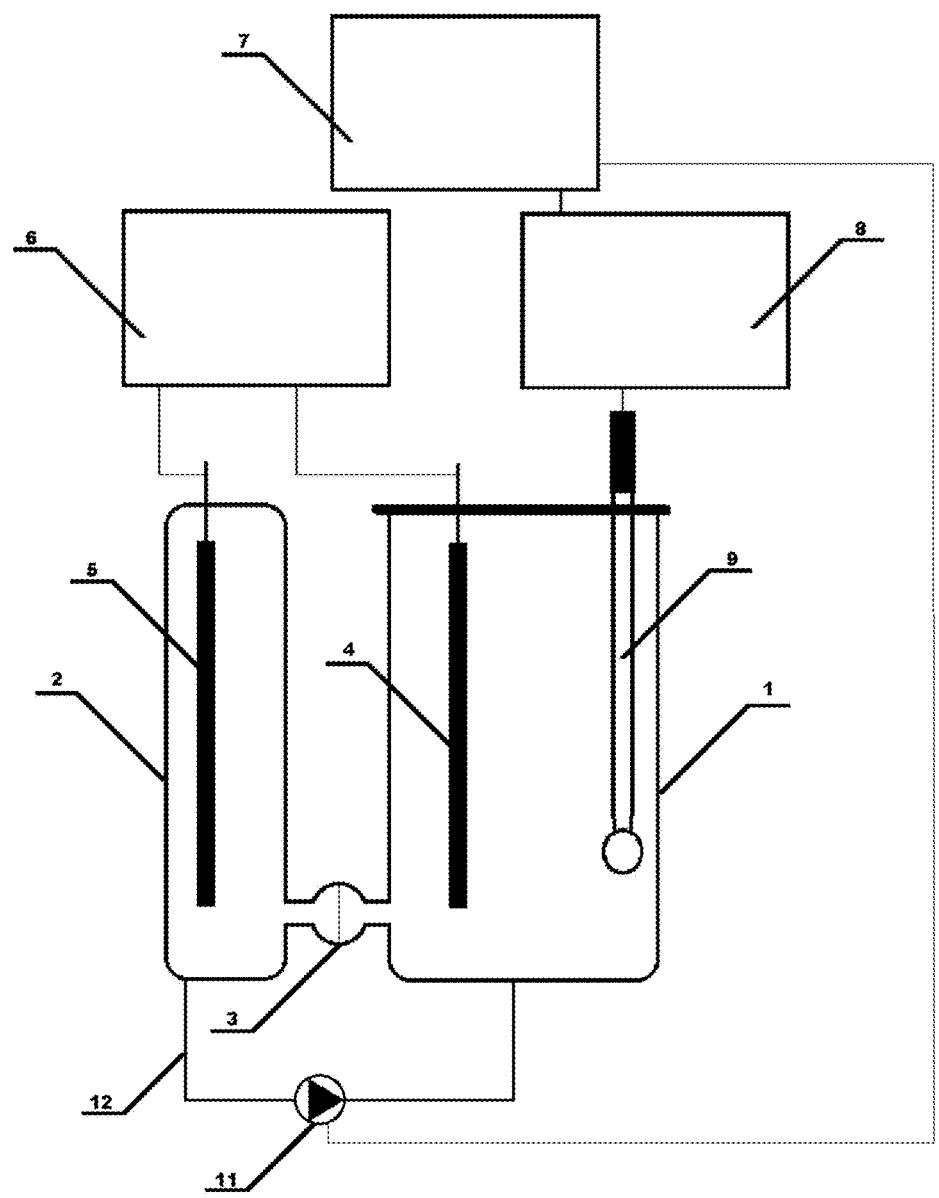
FIG. 3 is still another schematic view of an embodiment of the present invention.
Figure 4:
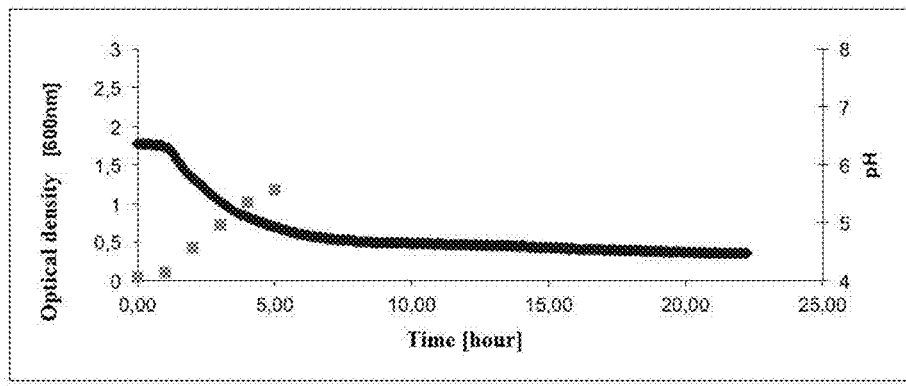
FIG. 4 is a graph illustration of optical density, time and pH according to an embodiment of the present invention.
Figure 5:
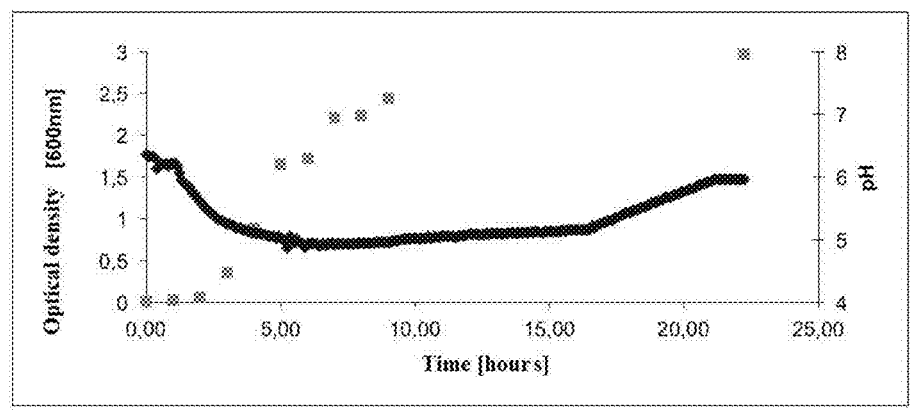
FIG. 5 is a graph illustration of optical density, time and pH according to an embodiment of the present invention.

The object of the invention is explained in the embodiment and the drawing, in which FIG. 1 shows a diagram of the workstation with a computer-controlled power supply, FIG. 2 a diagram of the workstation with a computer-controlled power supply with a rotating electrode, whereas FIG. 3 shows a diagram of the workstation with a power supply operating in a continuous mode, and a computer-controlled metering pump, FIG. 4 shows a plot of optical density (pink squares) versus time and pH as a function of time (dark blue line) for the control sample, FIG. 5 shows a plot of optical density (pink squares) versus time and pH as a function of time (dark blue line) for the proper sample.

Optical density is a measure of turbidity, which is directly proportional to the amount of bacteria in the culture medium.

EXAMPLE 1

Construction of the Reactor or System According to FIG. 1

In order to activate the reactor, fermentation tank 1 and auxiliary chamber 2 are filled with the medium (containing e.g. yeast extract—3 g/l, peptone—17 g/l, glucose—10 g/l, NaCl—5 g/l) containing nutrients and ions, such as: $Na^+$, $K^+$, $Ca^{2+}$, $Mg^{2+}$, $Zn^{2+}$, $Fe^{2+}$, $NH_4^+$, $SO_4^{2-}$, $HPO_4^{2-}$, $NO_3^-$, $HCO_3^-$. Then the medium is inoculated with a culture of microorganisms in order to initiate the fermentation process (e.g. *Escherichia coli* PCM 1144). When due to the accumulation of acidic metabolic products of microorganisms (organic acids in methane fermentation, lactic acid in bacterial cultures of the genus *Lactococcus*) pH in the culture is decreased, the signal of such a situation is registered by the glass electrode 9 and sent to the control unit 7. On the basis of the intensity of the received signal, the control unit 7 turns on a direct current power supply 6, which leads to polarization of the electrodes (electrode 4 negatively and the electrode 5 positively). Such a polarization of the electrodes leads to the generation of $OH^-$ ions around the electrode in the fermentation chamber 1 and $H^+$ ions in the auxiliary chamber 2, which in turn leads to increased pH in the fermentation chamber 1 and restoring the initial pH. After restoring pH setpoint, the control unit 7 turns off the direct current power supply 6 preventing too high alkalization of the solution in the fermentation tank 1. The voltage of the applied current is 50V (90 mA). The process is conducted at a temperature of 37° C. and at a stirring frequency of 1 Hz.

In the case of the culture of microorganisms which results in the alkalization of the medium, the control unit works in an analogous manner but with the difference that the polarization of the electrodes is reversed: the electrode located in the fermentation chamber is charged positively, whereas the electrode located in the auxiliary chamber is charged negatively. Such application of loads generates $H^+$ ions around the positive electrode in the fermentation chamber and decreases pH of the solution therein.

EXAMPLE 2

Reactor Constructed According to the Diagram in FIG. 2

A reactor for carrying out fermentation constructed according to FIG. 2 operates in a manner analogous to the set described in example 1, but with the difference that the installed electrode is also a mixer driven by a motor 10. This solution allows to reduce the layer of ions formed on the surface of the electrodes and reduce the resistance of the system.

EXAMPLE 3

Reactor Constructed According to the Diagram in FIG. 3

In the reactor constructed according to FIG. 3, during the fermentation, the direct current power supply 6 supplying current to the electrolysis reaction is always on. In the case of excessive flow of ions between the chambers, which leads to excessively rapid pH changes, information of which gets to the control unit 7 by means of a measuring system 8 and 9, the metering pump 11 is enabled, allowing the flow of liquid from the auxiliary chamber 2 into the fermentation chamber 1 through the dispensing connector 12, which reduces excessive pH changes.

EXAMPLE 4

A method according to the invention is carried out in the reactor comprising two fermentation chambers connected with a salt bridge 3, equipped with electrodes 4 and 5 and glass electrode 9 for pH measuring, metering pump 11 and dispensing connector 12. The reactor is connected to a power supply 6, the control unit 7 and the measuring system 8 and 9.

In order to activate the reactor, fermentation tank 1 and auxiliary chamber 2 are filled with the medium (containing e.g. yeast extract—3 g/l, peptone—17 g/l, glucose—10 g/l, NaCl—5 g/l) containing nutrients and ions, such as: $Na^+$, $K^+$, $Ca^{2+}$, $Mg^{2+}$, $Zn^{2+}$, $Fe^{2+}$, $NH_4^+$, $SO_4^{2-}$, $HPO_4^{2-}$, $NO_3^-$, $HCO_3^-$. Then the medium is inoculated with a culture of microorganisms (e.g. *Escherichia coli* PCM 1144) in order to initiate the fermentation process. When due to the accumulation of acidic metabolic products of microorganisms (organic acids in methane fermentation, lactic acid in bacterial cultures of the genus *Lactococcus*) pH in the culture is decreased, the signal of such a situation is registered by the glass electrode 9 and sent to the control unit 7. On the basis of the intensity of the received signal, the control unit 7 turns on a direct current power supply 6, which leads to the polarization of the electrodes (electrode 4 negatively and electrode 5 positively). Such a polarization of the electrodes leads to the generation of $OH^-$ ions around the electrode in the fermentation chamber 1 and $H^+$ ions in the auxiliary chamber 2, which in turn leads to increased pH in the fermentation chamber 1 and restoring the initial pH. After restoring pH setpoint, the control unit 7 turns off the direct current power supply 6 in order to prevent too high alkalization of the solution in the fermentation tank 1. The voltage of the applied current is 0.1 V. The process is conducted at a temperature of 37° C. and at a stirring frequency of 1 Hz.

In the case of the culture of microorganisms which results in the alkalization of the control unit, one should act in an analogous manner but with the difference that the polarization of the electrodes should be reversed: the electrode located in the fermentation chamber should be charged positively, whereas the electrode located in the auxiliary chamber should be charged negatively. Such application of loads generates $H^+$ ions around the positive electrode in the fermentation chamber and decreases pH of the solution therein.

We claim:

1. A method of pH controlling during electrolytic fermentation processes of organic substrates, said method comprising the following steps:
    placing, a medium, biological reagents and chemical reagents in a fermentation tank;
    placing a first electrode powered by a DC power supply in said fermentation tank;
    placing said medium in an auxiliary chamber, said auxiliary chamber being connected to said fermentation tank by a salt bridge;
    placing a second electrode in said auxiliary chamber;
    switching on constant voltage initiating electrolytic processes with a value from 0.1 to 50 V;
    generating H+ ions around said first electrode and OH− ions around said second electrode;
    placing a glass electrode in said fermentation tank:
    reading pH data of said medium, said biological reagents and said chemical reagents in said fermentation tank with said glass electrode; and
    changing power parameters of said first electrode and said second electrode according to a set pH value of said medium and said pH data of said medium, said biological reagents and said chemical reagents in said fermentation tank,
    wherein the step of changing power parameter comprises at least one of the following steps:
    switching said first electrode and said second electrode so as to generate H+ ions from said second electrode and OH− ions from said first electrode; and
    metering said medium from said auxiliary chamber into said fermentation tank chamber through a dispensing connector by a pump.

2. The method according to claim 1, wherein the step of changing power parameters comprises the step of switching said first electrode and said second electrode, said medium in said fermentation tank having pH<7.

3. The method according to claim 1, wherein the step of changing power parameters further comprises the step of: switching back said first electrode and said second electrode so as to generate H+ ions from said first electrode and OH− ions from said second electrode, said medium in said fermentation tank having pH>7.

4. The method according to claim 1, wherein said first electrode generates OH− ions when said medium in said fermentation tank has pH<7.

5. The method according to claim 1, wherein said second electrode generates H+ ions in said auxiliary chamber, when said medium in said fermentation tank has pH>7.

* * * * *